(12) United States Patent
Tlusty et al.

(10) Patent No.: US 10,456,603 B2
(45) Date of Patent: Oct. 29, 2019

(54) SYSTEMS AND METHODS FOR OPTIMIZING TRANSSKULL ACOUSTIC TREATMENT

(71) Applicants: Tal Tlusty, Zichron Ya'acov (IL); Shuki Vitek, Haifa (IL); Eyal Zadicario, Tel Aviv-Jaffa (IL)

(72) Inventors: Tal Tlusty, Zichron Ya'acov (IL); Shuki Vitek, Haifa (IL); Eyal Zadicario, Tel Aviv-Jaffa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 1334 days.

(21) Appl. No.: 14/566,040

(22) Filed: Dec. 10, 2014

(65) Prior Publication Data

US 2016/0184026 A1 Jun. 30, 2016

(51) Int. Cl.
*A61N 7/00* (2006.01)
*A61B 8/08* (2006.01)
*A61N 7/02* (2006.01)
*A61B 5/00* (2006.01)
*A61B 6/03* (2006.01)
*A61B 6/00* (2006.01)
*A61B 34/10* (2016.01)
(Continued)

(52) U.S. Cl.
CPC .............. *A61N 7/00* (2013.01); *A61B 5/0042* (2013.01); *A61B 6/032* (2013.01); *A61B 6/037* (2013.01); *A61B 6/501* (2013.01); *A61B 6/5217* (2013.01); *A61B 8/0816* (2013.01); *A61B 8/5223* (2013.01); *A61B 34/10* (2016.02); *A61N 7/02* (2013.01); *A61B 8/0808* (2013.01); *A61B 90/10* (2016.02); *A61B 2034/104* (2016.02); *A61B 2034/105* (2016.02); *A61B 2090/062* (2016.02); *A61B 2090/067* (2016.02); *A61N 2007/0021* (2013.01); *A61N 2007/0078* (2013.01); *A61N 2007/0095* (2013.01); *A61N 2007/025* (2013.01)

(58) Field of Classification Search
CPC .................. A61N 7/0002; A61N 7/022; A61N 2007/0004–0095; A61N 2007/025; A61N 2007/027
See application file for complete search history.

(56) References Cited

U.S. PATENT DOCUMENTS 7,215,806 B1 * 5/2007 Bechwati ................ G06T 5/007
378/21
8,603,014 B2 * 12/2013 Alleman .................. A61N 7/00
601/2

(Continued)

OTHER PUBLICATIONS

International Search Report and Written Opinion issued in a corresponding International Application No. PCT/IB2015/002442 dated Aug. 29, 2016.

(Continued)

*Primary Examiner* — Angela M Hoffa
(74) *Attorney, Agent, or Firm* — Morgan, Lewis & Bockius LLP

(57) ABSTRACT

Skull inhomogeneity may be quantified in accordance with the skull density measured in skull images acquired using a conventional imager; the quantified inhomogeneity may then be used to determine whether the patient is suitable for ultrasound treatment and/or determine parameters associated with the ultrasound transducer for optimizing transskull ultrasound treatment.

20 Claims, 8 Drawing Sheets

(51) Int. Cl.
*A61B 90/00* (2016.01)
*A61B 90/10* (2016.01)

(56) References Cited

U.S. PATENT DOCUMENTS

| | | | | |
|---|---|---|---|---|
| 8,617,073 | B2 * | 12/2013 | Prus | A61B 8/14 |
| | | | | 600/407 |
| 2003/0092987 | A1 | 5/2003 | Hynynen et al. | |
| 2006/0058670 | A1 | 3/2006 | Lin et al. | |
| 2006/0064082 | A1 * | 3/2006 | Bonutti | A61N 7/00 |
| | | | | 606/32 |
| 2007/0016050 | A1 * | 1/2007 | Moehring | A61B 8/06 |
| | | | | 600/454 |
| 2010/0016707 | A1 * | 1/2010 | Amara | A61B 5/02007 |
| | | | | 600/411 |
| 2010/0179425 | A1 * | 7/2010 | Zadicario | A61N 7/02 |
| | | | | 600/438 |
| 2010/0268088 | A1 * | 10/2010 | Prus | A61B 8/14 |
| | | | | 600/459 |
| 2011/0270136 | A1 | 11/2011 | Vitek et al. | |
| 2017/0188992 | A1 * | 7/2017 | O'Brien | A61B 8/0891 |

OTHER PUBLICATIONS

Jayachandran, et al., Automatic Detection of Brain Tumor in Magnetic Resonance Images using Multi-Texton Histogram and Support Vector Machine, Wiley Periodicals, Inc., vol. 23, 97-103 (2013).

\* cited by examiner

SYSTEMS AND METHODS FOR OPTIMIZING TRANSSKULL ACOUSTIC TREATMENT

FIELD OF THE INVENTION

The present invention relates, generally, to acoustic energy treatment and, more particularly, to systems and methods for optimizing the acoustic energy transmitted through a non-uniform tissue, such as the skull, during treatment.

BACKGROUND

Acoustic energy, such as ultrasound, penetrates well through soft tissues and, due to its short wavelengths, can be focused to spots with dimensions of a few millimeters. As a consequence of these properties, acoustic energy can and has been used for a variety of diagnostic and therapeutic medical purposes, including ultrasound imaging and non-invasive surgery of many parts of the body. For example, by heating diseased (e.g., cancerous) tissue using ultrasound, it is often possible to ablate the diseased portions without causing significant damage to surrounding healthy tissue.

The noninvasive nature of ultrasound surgery is particularly appealing for the treatment of brain tissue. Moreover, coherent, non-invasive focusing of ultrasound through the human skull has been considered as a tool for targeted drug delivery to the brain, improved thrombolytic stroke treatment, blood flow imaging, the detection of internal bleeding, and tomographic brain imaging. However, the human skull has been a barrier to the clinical realization of many of these applications. Impediments to transcranial procedures include strong attenuation and the distortions caused by irregularities in the skull's shape, density, and thickness, which contribute towards destroying the ultrasound focus and/or decreasing the ability to spatially register received diagnostic information.

Conventional approaches for overcoming the transskull focusing difficulties described above involve the use of receiving probes designed for catheter insertion into the brain to measure the amplitude and phase distortion caused by the skull; corrections to the focus are then made by adjusting the ultrasound beam emitted from a transducer array. Alternatively, a completely noninvasive approach uses imaging information (e.g., X-ray computed tomography (CT) or MRI volumetric images), rather than receiving probes, to estimate the thickness, density and geometry of the skull surfaces and to predict the wave distortion caused thereby.

While the conventional approaches may partially improve the ultrasound focus, predicting the effects on the ultrasound beam traversing the skull remains challenging because of the nature of the skull and its multiple-layered internal structure, which varies from patient to patient; this limits the effectiveness and efficiency of transskull ultrasound treatment using conventional approaches. As a result, patients having skull structures that result in poor ultrasound focusing properties may get limited benefit from the ultrasound therapy in compliance with safety standards that limit deliverable energy levels. Accordingly, there is a need for an approach that predicts the effectiveness of ultrasound treatment for individual patients, improves ultrasound focusing properties, and effectively delivers ultrasound energy to a target through individual patients' skulls.

SUMMARY

The present invention provides, in various embodiments, systems and methods for estimating transskull ultrasound focusing properties at the target region by analyzing the inhomogeneity of the inner multilayer structure of an individual patient's skull, and, based thereon, determining whether the patient is a suitable candidate for ultrasound treatment. If an affirmative determination is made, parameters associated with the ultrasound transducers may be adjusted in accordance with the observed skull inhomogeneity to improve the ultrasound focusing properties, thereby optimizing transskull ultrasound treatment. In one implementation, the inhomogeneity of the skull's structure and geometry is quantified at the microstructure level (i.e., with a feature length of a few micrometers, e.g., one, five or 10 micrometers) based on the skull density measured in CT images or images acquired using other approaches (e.g., magnetic resonance imaging with an ultra-short echo time). The quantified skull density (represented as the "skull density ratio" (SDR) herein) is utilized to predict ultrasound reflections and/or refractions traversing the skull of individual patients. Based on the prediction, the focusing properties of each beam (e.g., beam intensity, location and phase) at the target region can be estimated. For example, the ultrasound intensity transmitted through a skull region at the target region may inversely correlate with the SDR of the skull region, in which case the ultrasound energy actually delivered to the target region after traversing the skull region can be quantitatively determined based on the SDR. Accordingly, single transducer elements or groups of transducer elements may be activated or deactivated based on the associated SDRs to achieve optimal transducer efficiency and/or minimize unwanted heat absorption in the skull. In addition, parameters (e.g., intensities or phases) of the transducer elements may be adjusted in accordance with the SDRs to improve the focusing properties, such as the symmetry of the focus shape, and optimize the effectiveness of ultrasound treatment.

Accordingly, in a first aspect, the invention pertains to a method of predicting the likelihood of effective transskull ultrasound treatment for individual patients. In various embodiments, the method includes obtaining multiple images of a patient's skull, computationally determining a global parameter representing structural characteristics of the skull on multiple beam paths, and based at least in part on the global parameter, determining the likelihood of successful ultrasound treatment of the patient. In one implementation, each beam path extends from an ultrasound transducer element to the skull. In various embodiments, the method includes treating the patient with ultrasound if the determined global parameter exceeds a threshold value (e.g., 0.3). Of course, the lower the parameter value, the more time and delivered energy the treatment will require. Still, whether to actually perform the treatment depends on the severity of the patient's condition, the clinical desirability of treatment, the patient's ability to withstand the required duration, co-morbidities, etc. Accordingly, the global parameter is frequently used as one factor on which a treatment decision is based rather than the only factor.

The method may further include computationally determining multiple local parameters; each local parameter represents local structural skull characteristics on one of the beam paths and the global parameter is determined based on at least some of the local parameters. In addition, the method may include assigning a weighting factor to each of the local parameters based on the incidence angle of the associated beam path through the skull; the global parameter is determined based on a weighted average of the at least some of the local parameters. For example, a weighting factor of one may be assigned to each local parameter corresponding to a beam path having an incidence angle smaller than a critical angle and a weighting factor of zero may be assigned to each local parameter corresponding to a beam path having an incidence angle larger than the critical angle. Alternatively, the weighting factor may be determined based on a logistic function. In one embodiment, the logistic function satisfies the following equation:

$$L_i = 1 - \frac{1}{1 + e^{-(\theta_i - \mu)/\sigma}},$$

where $L_i$ denotes the logistic function, $\theta_i$ denotes the incidence angle of the beam path from a transducer element i to the skull, $\sigma$ denotes a steepness factor representing deviation of a curve of the logistic function from a step function, and $\mu$ denotes an inflection point of the logistic function.

In various embodiments, the local parameter includes a local skull density ratio; the local skull density ratio is determined based on an intensity profile of the images. The images may be acquired using a computer tomography (CT) device, a magnetic resonance imaging device, a positron emission tomography (PET) device, a single-photon emission computed tomography (SPECT) device, and/or an ultrasonography device. Additionally, the global parameter may include a global skull density ratio. Further, in some embodiments, the method may include identifying a position of a treatment target area in the images, determining positions of multiple ultrasound transducer elements for transmitting ultrasound energy to the target area, and determining the beam paths based at least in part on the positions of the transducer elements and the target area.

In another aspect, the invention relates to a system for predicting a likelihood of effective transskull ultrasound treatment for individual patients and, in some implementations, controlling or limiting treatment based thereon. In various embodiments, the system includes an imaging system for obtaining multiple images of a patient's skull, and a controller that is operably coupled to the imaging system and configured to (i) computationally determine a global parameter representing structural characteristics of the skull on multiple beam paths and (ii) based at least in part on the global parameter, determine the likelihood of successful ultrasound treatment of the patient. Each beam path extends from an ultrasound transducer element to the skull. In various embodiments, the controller is configured to activate at least some of the transducer elements to treat the patient based at least in part on the determined global parameter; for example, if the parameter value exceeds a threshold value (e.g., 0.4), treatment may proceed automatically or, conversely, if the parameter is below the threshold value, treatment may be automatically prevented (generally subject to a clinician's prerogative to override the determination and proceed with treatment). As explained above, the global parameter may be only one factor on which a treatment decision is based rather than the only factor; accordingly, the final decision whether to proceed with treatment may depend on the clinical status of a specific patient (the need for treatment to preserve overall health, the patient's likely tolerance to high energy doses, etc.) and the overall probability, given the patient's clinical status, of achieving adequate treatment results.

In addition, the controller may be configured to computationally determine multiple local parameters; each local parameter represents local structural skull characteristics on one of the beam paths and the global parameter is determined based on at least some of the local parameters. The controller may assign a weighting factor to each of the local parameters based on an incidence angle of the associated beam path through the skull; the global parameter is determined based on a weighted average of the at least some of the local parameters. For example, the controller may assign a weighting factor of one to each local parameter corresponding to a beam path having an incidence angle smaller than a critical angle and a weighting factor of zero to each local parameter corresponding to a beam path having an incidence angle larger than the critical angle. Alternatively, the controller may determine the weighting factor based on a logistic function. For example, the logistic function may satisfy the following equation:

$$L_i = 1 - \frac{1}{1 + e^{-(\theta_i - \mu)/\sigma}},$$

where $L_i$ denotes the logistic function, $\theta_i$ denotes the incidence angle of the beam path from a transducer element i to the skull, $\sigma$ denotes a steepness factor representing deviation of a curve of the logistic function from a step function, and $\mu$ denotes an inflection point of the logistic function.

In some embodiments, the local parameter includes a local skull density ratio. The controller is configured to determine the local skull density ratio based on an intensity profile of the obtained images. The imaging system may include a computer tomography (CT) device, a magnetic resonance imaging device, a positron emission tomography (PET) device, a single-photon emission computed tomography (SPECT) device, and/or an ultrasonography device. In various embodiments, the controller is configured to identify a position of a treatment target area in the images; determine positions of the ultrasound transducer elements for transmitting ultrasound energy to the target area; and determine the beam paths based at least in part on the positions of the transducer elements and the target area.

Still another aspect of the invention relates to a method for transskull ultrasound treatment with optimized focusing properties at a target region. In various embodiments, the method includes obtaining multiple images of a patient's skull; computationally determining multiple local parameters, each local parameter representing structural characteristics of a local skull region on a beam path from a transducer element; and activating at least some of the transducer elements with transmission powers determined based at least in part on the local parameters associated therewith.

The transmission power from each transducer element may correlate inversely with the associated local parameter. For example, the transmission power from each transducer element may satisfy the following equation:

$$Power_i = \text{total applied power} \times \frac{1/LP_i}{\sum_{i=1}^{N} LP_i},$$

where $Power_i$ denotes transmission power of a transducer element i, N denotes a number of activated transducer elements, total applied power denotes a total power applied by the activated transducer elements, and $LP_i$ denotes the local parameter associated with the transducer element i.

In some embodiments, the local parameter includes a local skull density ratio; the local skull density ratio is determined based on an intensity profile of the images. The images may be acquired using a computer tomography (CT) device, a magnetic resonance imaging device, a positron emission tomography (PET) device, a single-photon emission computed tomography (SPECT) device, and/or an ultrasonography device. In various embodiments, the transducer element may be activated if the local parameter associated therewith is above a threshold. The threshold may be empirically determined based on a retrospective study of skulls of patients who have undergone ultrasound treatment. In one implementation, the method further includes identifying a position of a treatment target area in the images; determining positions of the ultrasound transducer elements for transmitting ultrasound energy to the target area; and determining the beam path from each transducer element to the skull based on the positions of the transducer element and the target area.

In yet another aspect, the invention relates to a system for transskull ultrasound treatment with optimized focusing properties at a target region. In various embodiments, the system includes an imaging system for obtaining multiple images of a patient's skull; a controller that is operably coupled to the imaging system and configured to (i) identify a position of a treatment target area in the images, and (ii) computationally determine multiple local parameters, each local parameter representing structural characteristics of a local skull region on a beam path from a transducer element; and drive circuitry that is coupled to the controller for activating at least some of the transducer elements with transmission powers determined based at least in part on the local parameters associated therewith.

In some embodiments, the drive circuitry is configured to drive each transducer element with a transmission power correlating inversely with the associated local parameter. For example, the transmission power from each transducer element satisfies the following equation:

$$Power_i = \text{total applied power} \times \frac{1/LP_i}{\sum_{i=1}^{N} LP_i},$$

where $Power_i$ denotes transmission power of a transducer element i, N denotes a number of activated transducer elements, total applied power denotes a total power applied by the activated transducer elements, and $LP_i$ denotes the local parameter associated with the transducer element i.

In various embodiments, the local parameter includes a local skull density ratio; the controller is configured to determine the local skull density ratio based on an intensity profile of the images. The imaging system may include a computer tomography (CT) device, a magnetic resonance imaging device, a positron emission tomography (PET) device, a single-photon emission computed tomography (SPECT) device, and/or an ultrasonography device. In various embodiments, the drive circuitry is configured to activate the transducer element if the local parameter associated therewith is above a threshold. The controller may empirically determine the threshold based on a retrospective study on skulls of patients who have undergone ultrasound treatment. In some embodiments, the controller is further configured to determine positions of the ultrasound transducer elements for transmitting ultrasound energy to the target area, and determine the beam path from each transducer element to the skull based on the positions of the transducer element and the target area.

As used herein, the terms "approximately" and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention in conjunction with the drawings, wherein.

DETAILED DESCRIPTION

Figure 1:
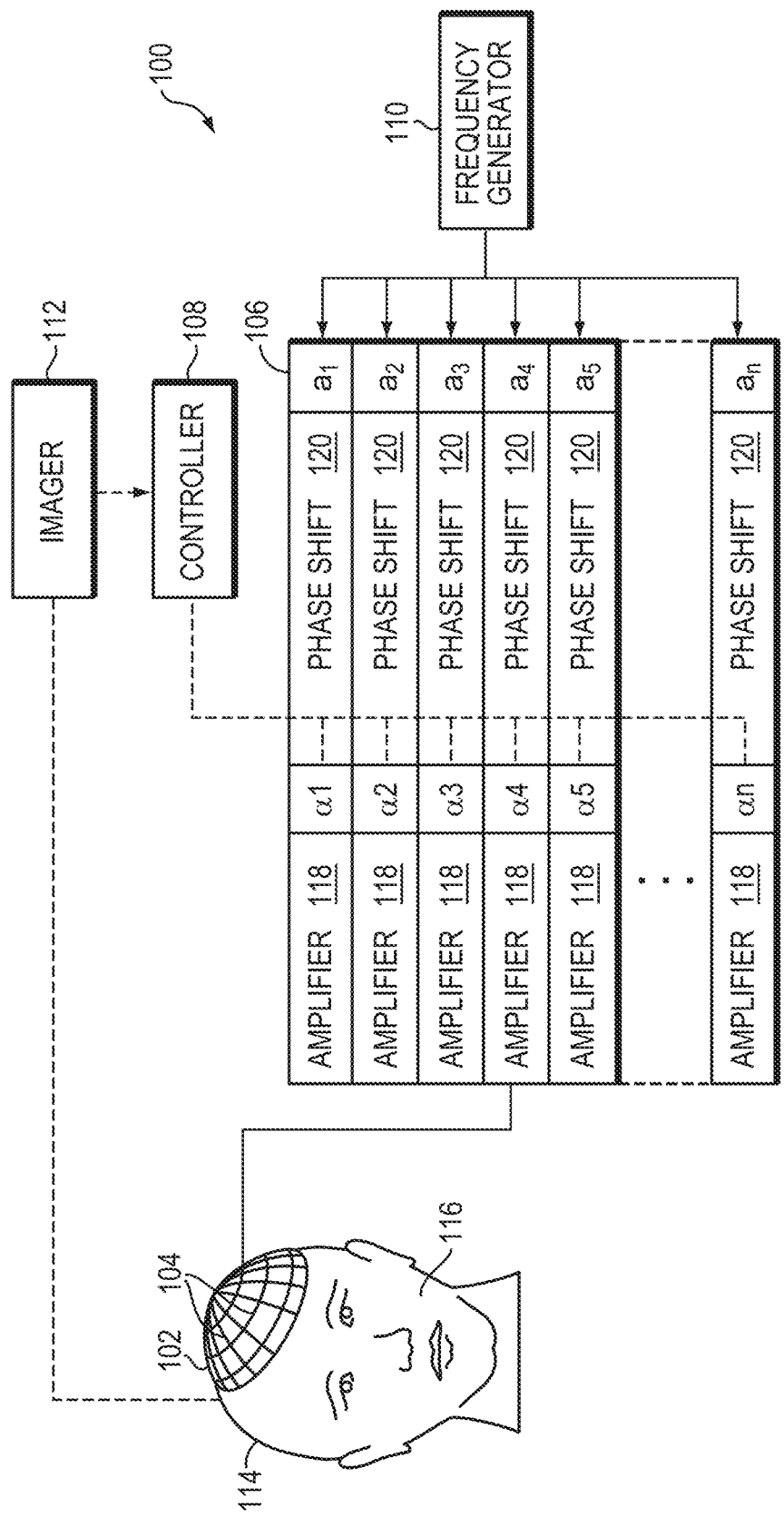
FIG. 1 is a schematic diagram of a system for focusing ultrasound in accordance with various embodiments of the present invention.

FIG. 1 illustrates an exemplary ultrasound therapy system 100 for focusing ultrasound onto a patient's brain through the skull. The system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull 114 of a patient 116.

The array 102 may have a curved (e.g., spherical or parabolic) shape suitable for placing it on the surface of the skull 114, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezocomposite materials, or generally any materials capable of converting electrical energy to acoustic energy, may also be used. To assure maximum power transfer to the transducer elements 104, the elements 104 may be configured for electrical resonance at 50 W, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto a selected region of the patient's brain, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus. In certain embodiments, the computation is based on detailed information about the characteristics (e.g., structure, thickness, density, etc.) of the skull 114. Such information may be obtained from the imager 112. Image acquisition may be three-dimensional or, alternatively, the imager 112 may provide a set of two-dimensional images suitable for reconstructing a three-dimensional image of the skull 114 from which thicknesses and densities can be inferred. Image-manipulation functionality may be implemented in the imager 112, in the controller 108, or in a separate device.

System 100 may be modified in various ways within the scope of the invention. For example, for diagnostic applications, the system may further include a detector device (not shown) that measures transmitted or reflected ultrasound, and which may provide the signals it receives to the controller 108 for further processing. The reflection and transmission signals may also be used as feedback for the phase and amplitude adjustments of the beamformer 106. The system 100 may contain a positioner for arranging the array 102 of transducer elements 104 with respect to the patient's skull 114. In order to apply ultrasound therapy to body parts other than the brain, the transducer array 102 may take a different, e.g., a cylindrical, shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
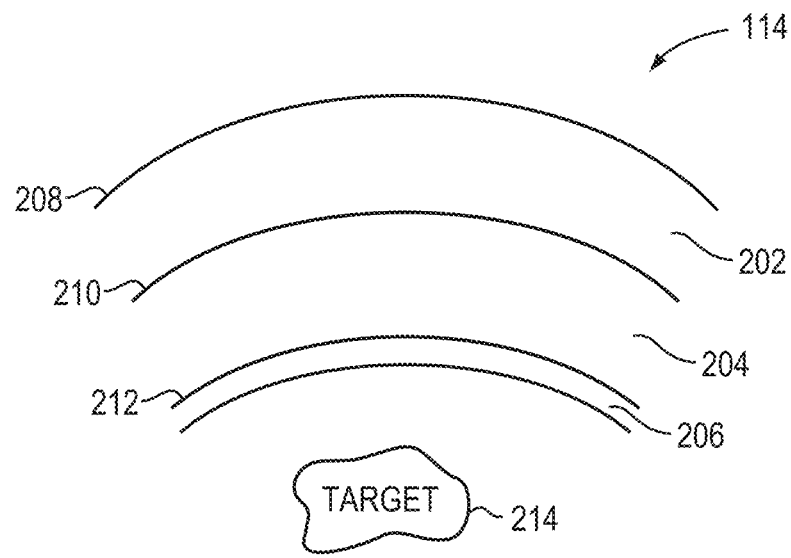
FIG. 2A schematically illustrates tissue layers of a human skull.

Referring to FIG. 2A, a typical human skull 114 has multiple tissue layers, including an external layer 202, a bone marrow layer 204, and an internal layer or cortex 206; each layer of the skull 114 may be highly irregular in shape, thickness and density, and unique to a patient. As a result, when the ultrasound waves emitted from the system 100 encounter the skull 114, part of the incident acoustic energy may be reflected at the interfaces 208, 210, 212; the remaining energy may be partially absorbed, and partially refracted and propagated through the skull 114 depending on the frequency of the waves and the structural inhomogeneity of the skull 114. Because the frequency of the ultrasound waves is controllable, the effects of wave propagation through the skull 114 and the focusing properties at the target region 214 may be accurately estimated in accordance with the structural inhomogeneity of the skull 114 (e.g., thickness, density, and/or shape of each layer 202-206). In various embodiments, the structural inhomogeneity is characterized using an indicator that can be quantified at the microstructure level (i.e., having a sensitivity or feature length on the order of a few micrometers, e.g., one, five or 10 micrometers) of the skull 114; the indicator is determined based on the skull density measured in images acquired using the imager 112.

Figure 2B:
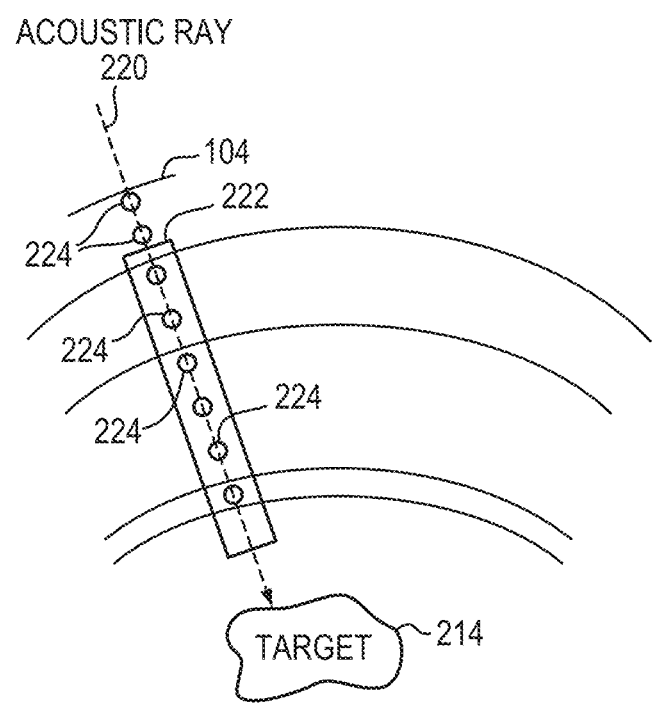
FIG. 2B illustrates image analysis used to determine anatomical characteristics of a patient's skull in accordance with various embodiments of the present invention.
Figure 2C:
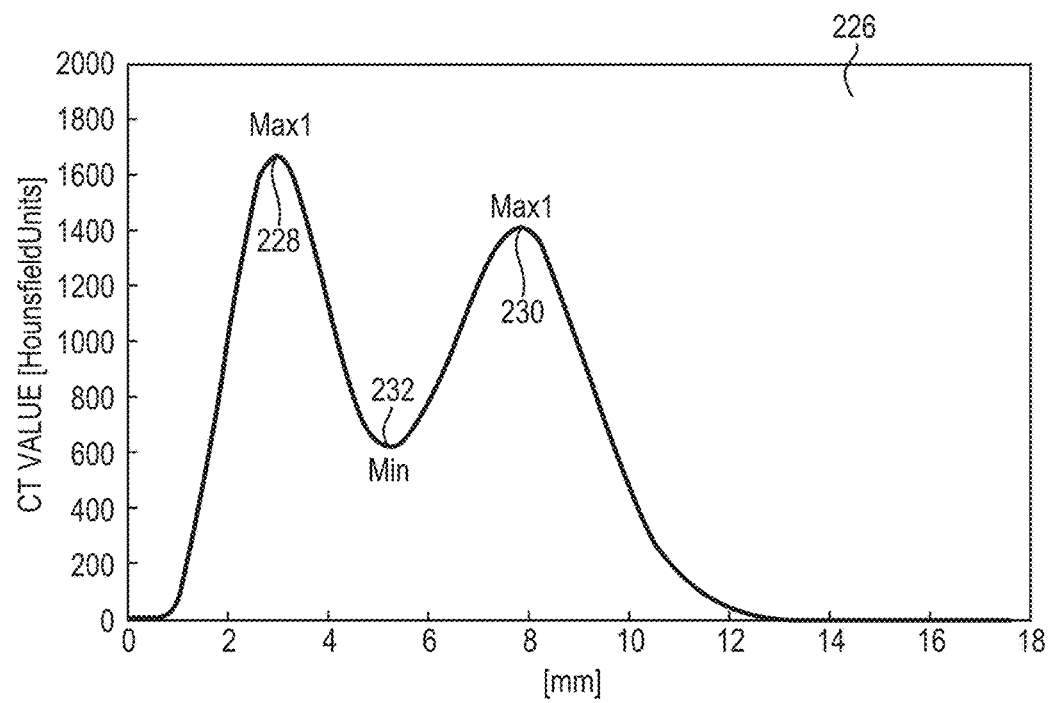
FIG. 2C illustrates an exemplary CT intensity profile of a skull region in accordance with various embodiments of the present invention.

For example, the indicator may be a quantified skull density ratio (SDR) created using a skull CT intensity profile obtained from CT images. FIG. 2B illustrates an acoustic ray 220 traveling through a CT volume 222 representing a skull region at the target region 214 in the brain. In some embodiments, pixel values 224 along the path of the ray 220 and spanning the distance between the target region 214 and each transducer element 104 are determined and arranged to form a CT intensity profile for each skull region 222. The pixel values 224 may represent, for example, the absorption of the x-rays in the skull region 222 (typically measured in "Hounsfield units," "CT values," or "CT numbers"). For example, referring to FIG. 2C, in a CT intensity profile 226, the external layer 202 and internal cortex layer 206 of a skull region 222 passed by the acoustic ray 220 may have higher CT values, i.e., local maxima 228 and 230, respectively; whereas the layer therebetween may have a lower CT value (i.e., local minimum 232). In one implementation, the local structural inhomogeneity of the skull region 222 on the acoustic ray path between a transducer element i and the target region 214 is characterized by a ratio (or a "local" SDR) of the local minimum CT value 232 to an average of the local maximum CT values 228, 230; the local SDR can be expressed as:

$$SDR_i = \frac{CT_{min}}{\frac{1}{2}(CT_{max1} + CT_{max2})}$$

for each transducer element i.

Thus, the local SDR may be used to create a local geometric characteristic mapping of the skull 114.

To determine the efficiency and effectiveness of ultrasound treatment, the structural inhomogeneity of the entire skull region covered by the transducer array 102 may be evaluated. In one embodiment, a local SDR for each transducer element 104 covering a skull region is obtained and analyzed, and a similarity level associated with the local SDR is assigned based on the comparison with SDR statistics of the skulls of patients who have successfully undergone the ultrasound treatment previously. If a majority (e.g., more than 50%) of the local SDRs for the transducer array 102 has similarity levels above a threshold, the patient is considered to be a candidate for effective ultrasound treatment within applicable safety guidelines. In another embodiment, a single value, such as a "global" SDR, is calculated based on a collection of the local SDRs; the global SDR can then be used to determine a likelihood of successful ultrasound treatment.

Figure 3A:
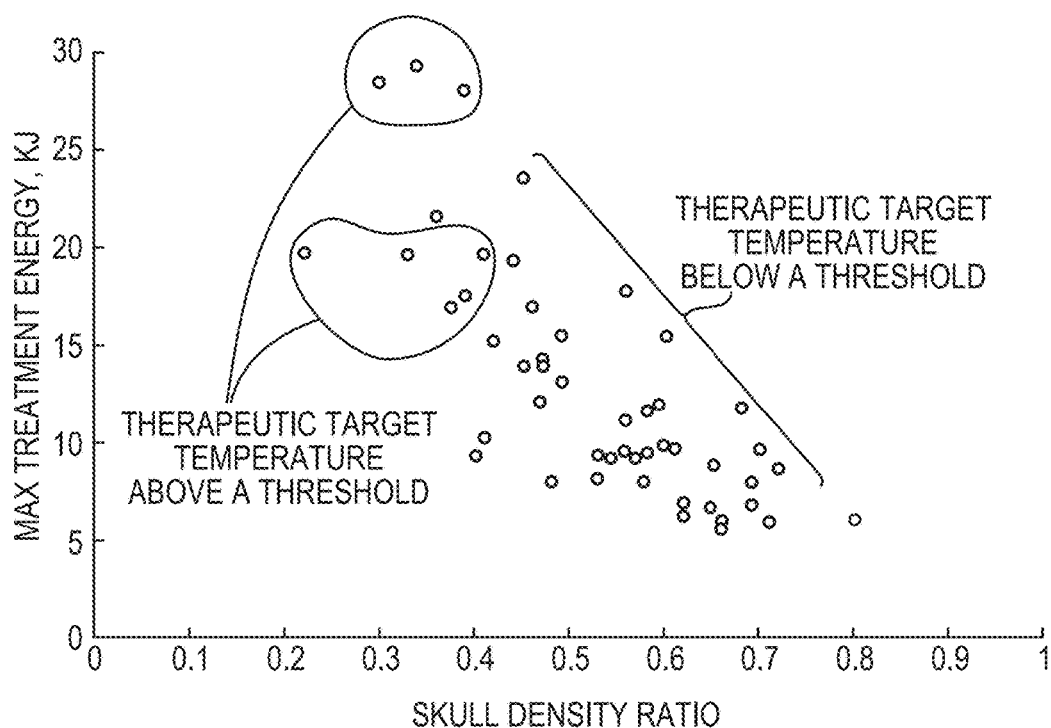
FIG. 3A depicts a relationship between global SDRs and maximum ultrasound energies applied during treatment for generating a therapeutic temperature at the target region in accordance with various embodiments of the present invention.

FIG. 3A depicts the relationship between global SDRs and maximum ultrasound energies required during treatment for generating a therapeutic temperature at the target region based upon a study of 50 patients. As shown, patients' skulls having smaller global SDRs generally require more energy transmitted from the transducer elements 104 to reach the therapeutic temperature at the target region 214. In addition, patients having skulls with global SDRs of less than 0.4 experienced failed treatment because therapeutic target temperatures were not reached at safe transmitted power levels. Accordingly, in various embodiments, the computed global SDR of a candidate patient is compared with the global SDR values of patients previously treated with ultrasound (for example, as statistics depicted in FIG. 3A) for determining the likelihood of successful treatment. This approach may expedite the patient evaluation process since only one single value is concerned. The global SDR, for example, may be as simple as an average of all local SDRs for the transducer elements 104 covering the skull. It is, however, well-known that some ultrasound waves may not be transmitted through the skull if their incidence angles on the exterior surface of the skull are greater than the critical angle (i.e., the angle above which acoustic rays are mostly reflected rather than traversed). In one embodiment, transducer elements 104 emitting such waves are deactivated. As a result, local SDRs corresponding to the deactivated transducer elements are discarded and the global SDR is determined based on the local SDRs corresponding to the activated transducer elements. This approach thus utilizes a step weight function assigned to the local SDRs in accordance with the incidence angles of the ultrasound waves emitted from the corresponding transducer elements i.e., a weighting factor of one is assigned to local SDRs corresponding to elements that deliver more energy to the target (i.e., having incidence angles below the critical angle), and a weighting factor of zero is assigned to local SDR corresponding to elements that deliver less energy to the target (i.e., having incidence angles above the critical angle).

Figure 3B:
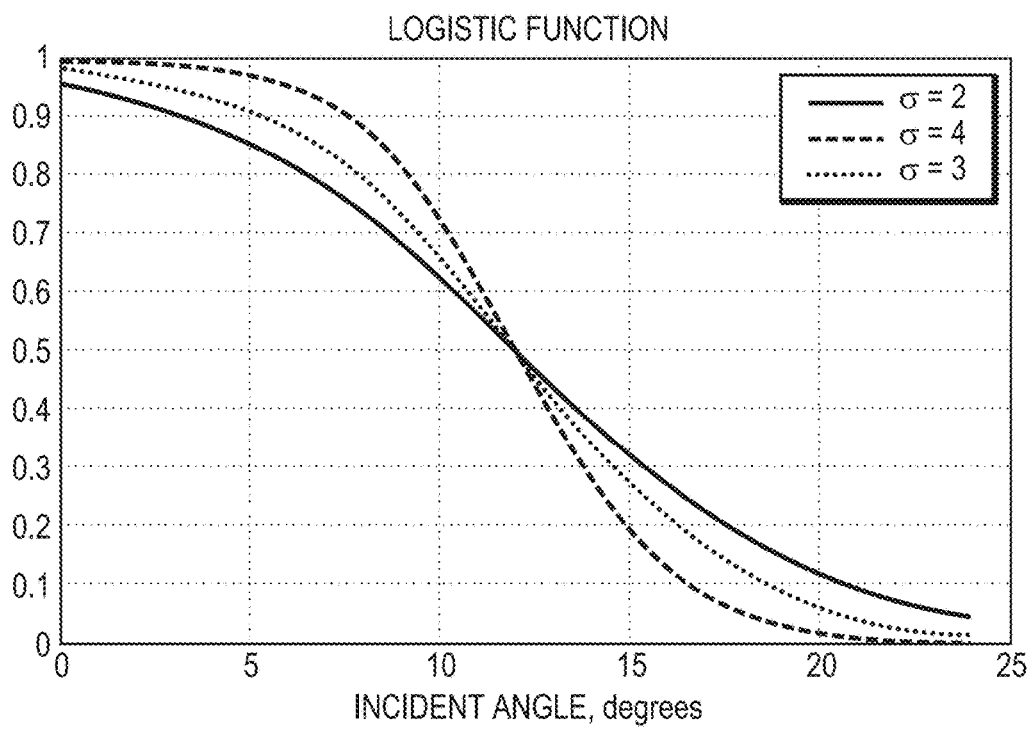
FIG. 3B shows a plot of a logistic function dependent on the incidence angle in accordance with various embodiments of the present invention.

Additionally, it is known that a gradual degradation in both ultrasound energy transmission through the skull 114 and accuracy of phase prediction at the target region 214 may occur as the incidence angle increases; as a result, ultrasound waves having incidence angles below the critical angle by a few degrees may still contribute little to the focal intensity. Therefore, to further improve the skull evaluation criterion, the step weight function as described above may be replaced with a function that has a smooth, continuous form at the critical angle. In one embodiment, the weight function, $W_i$, is defined as:

$$W_i = N \frac{L_i}{\sum_{i=1}^{N} L_i},$$

where N is the total number of the transducer elements, and $L_i$ is a logistic function that can be expressed as:

$$L_i = 1 - \frac{1}{1 + e^{-(\theta_i - \mu)/\sigma}},$$

where $\theta_i$ denotes the incidence angle of the ultrasound wave transmitted from transducer element i to the skull, $\sigma$ is a steepness factor representing the curve deviation of the logistic function from a step function, and $\mu$ is the inflection point of the curve. The values of $\sigma$ and $\mu$ may be empirically determined based on retrospective study of the patients experienced ultrasound treatment. In some embodiments, $\sigma$ can be chosen in a range between 1 and infinity and $\mu$ can be chosen in a range between 8 and 18. FIG. 3B depicts a plot of logistic functions dependent on incidence angles for various values of $\sigma$ at $\mu=12$. Although the weight function herein is defined using a logistic function, any other functions (for example, sigmoidal functions) with adjustable parameters suitable for defining a weight function may also be utilized in the present invention. Once the weight function is determined, the global SDR may be computed as a weighted average of the local SDRs using the weight function:

$$\text{global } SDR = \frac{1}{N} \sum_{i=1}^{N} W_i \times SDR_i,$$

In a preferred embodiment, each transducer element 104 transmits ultrasound waves onto a skull patch having an area of 5×5 mm² Because the skull structure on the patch may vary at different places, each patch may be divided into multiple segments, each corresponding to a CT region passed by the acoustic ray; a local SDR for each patch may then be computed as an average of the local SDRs of the multiple patch segments (or CT regions), i.e., $$SDR_i = \frac{1}{M} \sum_{j=1}^{M} SDR_{ij},$$

where M is the number of segments in each patch and $SDR_{ij}$ denotes the local SDR of each patch segment. Accordingly, the global SDR may be computed as:

$$\text{global } SDR = \frac{1}{NM} \sum_{i=1}^{N} W_i \sum_{j=1}^{M} SDR_{ij},$$

The number of segments, M, on each patch may depend on the distance correlation of the anatomical structure of different skull segments and/or the resolution of images acquired using imager 112. In a preferred embodiment, the area of each segment is equal to the square of the image resolution; as a result, M is derived by dividing the patch area by the square of the image resolution. For example, if a CT image has a resolution of 1 mm, a patch having an area of 5×5 mm² may be divided into 25 segments, each having a local $SDR_{ij}$.

The global SDR of a patient may be compared with the global SDRs of patients who have been previously treated with ultrasound in order to determine the likelihood of successful treatment. For example, referring again to FIG. 3A, in the retrospective study, patients having global SDRs above a threshold (e.g., 0.41) may have had successful treatment (e.g., more than 50% of the tumor tissue was ablated) because more energy can be delivered to the target region 214 passing through the skull 114; whereas patients having global SDRs below the threshold may have had less effective results since less energy is transmitted through the skull 114. Because the threshold may be determined based on both ex-vivo experimental lab results and treatment data analysis, the current invention provides a reliable approach to determine whether a patient is suitable for ultrasound treatment.

Figure 4:
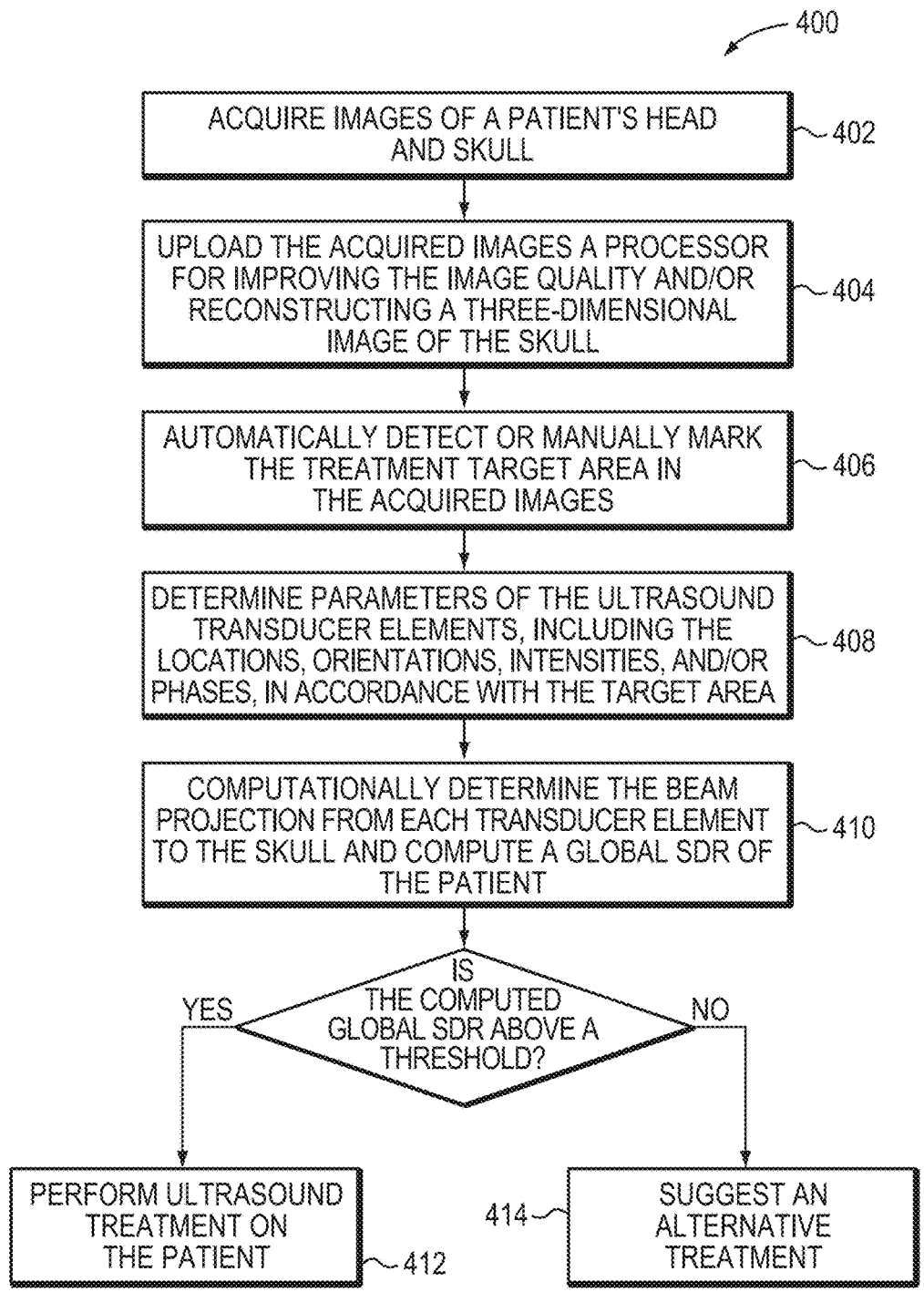
FIG. 4 is a flow chart illustrating an approach for predicting the likelihood of effective ultrasound treatment for individual patients in accordance with various embodiments of the present invention.

A representative method 400 illustrating the approach of estimating the likelihood of successful ultrasound treatment for individual patients in accordance with various embodiments of the current invention is shown in FIG. 4. In a first step 402, images of a patient's head and entire skull are acquired using the imager 112. In a second step 404, the acquired images are uploaded to the controller 108 that processes the images (e.g., by applying a conventional imaging filter, such as a bone filter) to improve the image quality and/or reconstruct a three-dimensional image of the skull. In a third step 406, the treatment target area in the acquired images may be automatically detected or manually marked by an operator. In a fourth step 408, the controller 108 may determine parameters of the ultrasound transducer elements 104, including the locations, orientations, intensities, and/or phases, in accordance with the location of the target area such that the transducer elements 104 can collectively produce a focused ultrasonic beam at the target. In a fifth step 410, the controller 108 may compute the beam projection from each transducer element 104 to the skull based on the positions of the transducer element and the target region, and the image data set as described above; a global SDR of the patient can then be computed. If the computed global SDR is above a threshold (which may be determined based on the global SDRs of patients having effective and/or ineffective ultrasound treatment), the ultrasound treatment is performed on the patient (step 412). If, however, the computed global SDR is below the threshold, the patient is suggested to seek an alternative treatment (step 414).

Figure 5A:
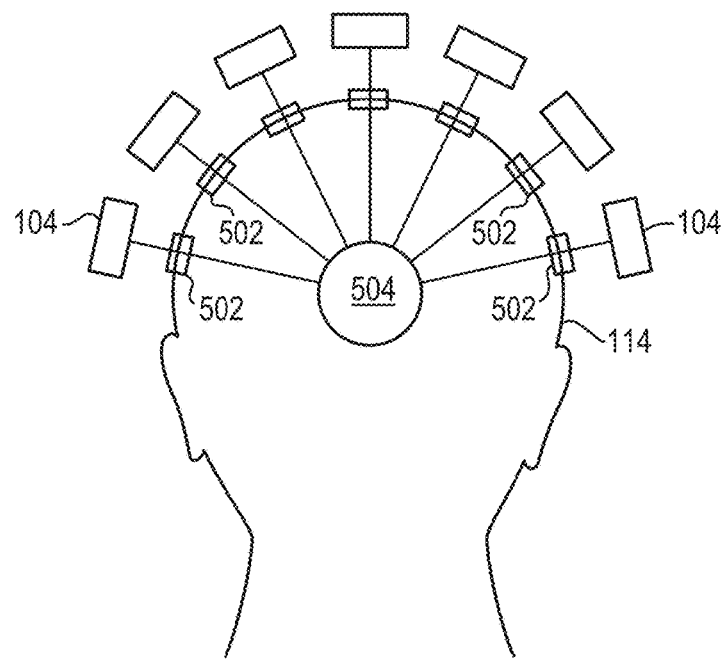
FIG. 5A depicts multiple skull regions, each corresponding to a particular transducer element or grouping of elements in accordance with various embodiments of the present invention.
Figure 5B:
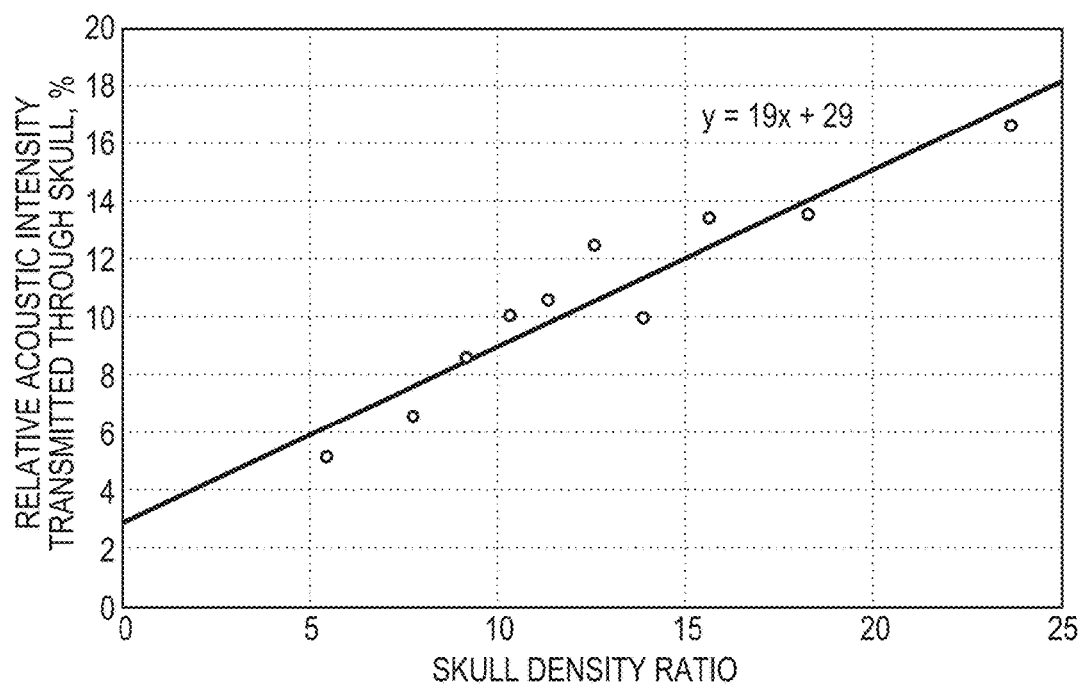
FIG. 5B depicts a relationship between SDRs and ultrasound intensities transmitted through the skull associated with the SDRs in accordance with various embodiments of the present invention.

In various embodiments, once the patient is determined to be suitable for an ultrasound treatment, an optimal treatment plan may be prepared based on the local SDRs of the patient's skull. Referring to FIG. 5A, the skull 114 can be defined as having more than one region 502, each of which may be related to or correspond to a particular transducer element 104 or grouping of elements. The ultrasound focus 504 may be created by beams emitted from the transducer elements 104, traversing various skull regions 502 from different directions and finally converging at the target region. It is desirable that the power amplitudes of the beams from all skull regions 502 are substantially uniform at the focus in order to minimize focus distortion and maximize the shape symmetry of the focus 504. Generating an ultrasound focus having a symmetric shape at the target region may be critical for treatment of brain tumors; this is because the target region may be near vital structures, which can be damaged by a distorted focus. Because different skull regions 502 may allow different amounts of energy to travel therethrough, a geometric characteristic mapping of the skull created by the local SDRs may be utilized to achieve optimized focusing properties, such as a symmetric shape of the focus, at the target region. Referring to FIG. 5B, the local SDR may positively correlate with the acoustic energy at the focus after the ultrasound waves travel through the skull. In other words, in a skull region having a higher local SDR, a larger portion of the energy transmitted by the transducer element 104 is delivered to the focus 504; this may result in reduced transmission energy requirements from the associated transducer element 104. Conversely, in a skull region having a lower local SDR, because a smaller portion of the energy is delivered to the focus 504, an increased transmission energy from the transducer element 104 may be required.

Accordingly, in one embodiment, if the local SDR is below a threshold (e.g., 0.3, or another value that may be determined based on a retrospective study of the patients who have undergone ultrasound treatment), the ultrasound traversal through the skull 114 is deemed ineffective. Therefore, the transducer element 104 corresponding to the small local SDR is deactivated to optimize the transducer efficiency. Deactivation of the non-contributing elements may have other benefits, such as minimizing skull heating and reducing overall transmission power required by the transducer array 102. For the transducer elements 104 that are determined to be active, their associated local SDRs may be used to obtain approximately equal-intensity contributions at the focus, thereby creating a symmetric focus shape. To achieve this, an SDR-weighted approach may be used. For example, transducer elements having lower local SDRs (i.e., facing denser areas of the skull and having less energy transmitted therethrough) may transmit higher powers than those having higher local SDRs. In one embodiment, the power transmitted from each transducer element 104 may inversely correlate to the local SDR and be determined in accordance with the following formula:

$$Power_i = \text{total applied power} \times \frac{1/SDR_i}{\sum_{i=1}^{N} SDR_i},$$

where Power$_i$ denotes the power transmitted by the transducer element i.

Figure 6A:
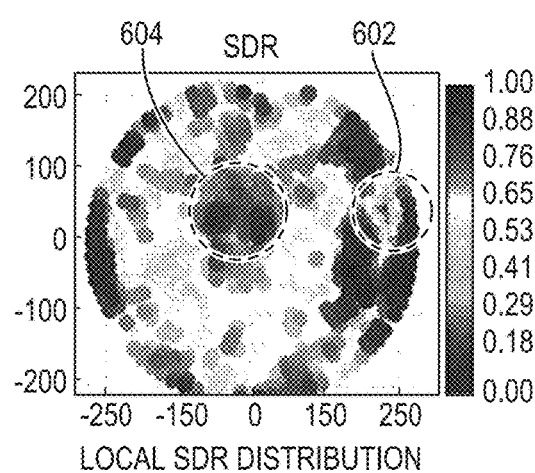
FIG. 6A depicts a planar local SDR distribution computed from the CT data of a patient's skull in accordance with various embodiments of the present invention.
Figure 6B:
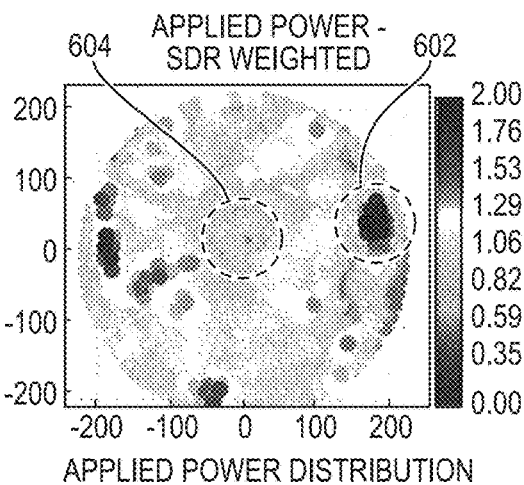
FIG. 6B depicts a transmitted power map of the transducer elements, where the applied power of each transducer element is determined using an SDR-weighted approach in accordance with various embodiments of the present invention.
Figure 6D:
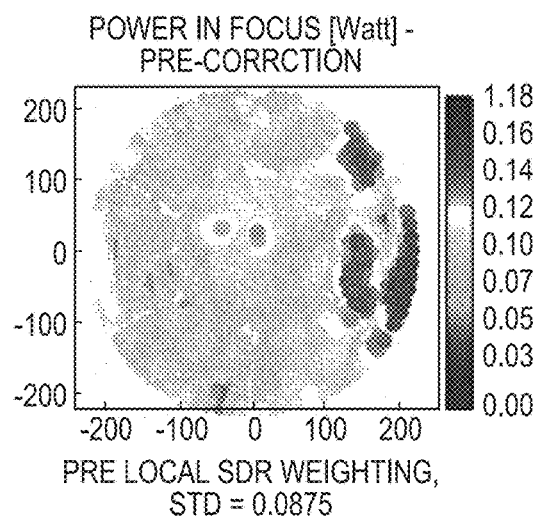
FIG. 6D illustrates non-uniform power contributions from the transducer elements at the focal spot without using the SDR-weighted approach.
Figure 6C:
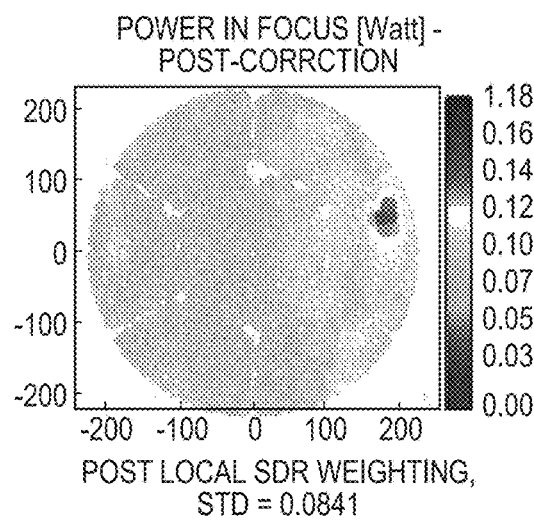
FIG. 6C illustrates uniform power contributions from the transducer elements at the focal spot using an SDR-weighted approach in accordance with various embodiments of the present invention.

FIG. 6A depicts a planar local SDR distribution computed from the CT data of a patient's skull. As shown, the skull structure represented by the SDRs is highly inhomogeneous. FIG. 6B depicts the applied power of each transducer element 104 computed using the above-described formula. A higher power may be transmitted to the area 602 having a lower SDR, and a lower power may be transmitted to the area 604 having a higher SDR. As a result, referring to FIG. 6C, the power contribution from each transducer element at the focal spot is substantially uniform. By contrast, if the applied power of each element is determined simply by dividing the total power of the transducer array 102 by the number of activated transducer elements (i.e., power$_i$=total applied power/N$_{active}$), the power contributions from the transducer elements at the focus 504 may be relatively non-uniform (FIG. 6D).

Figure 7:
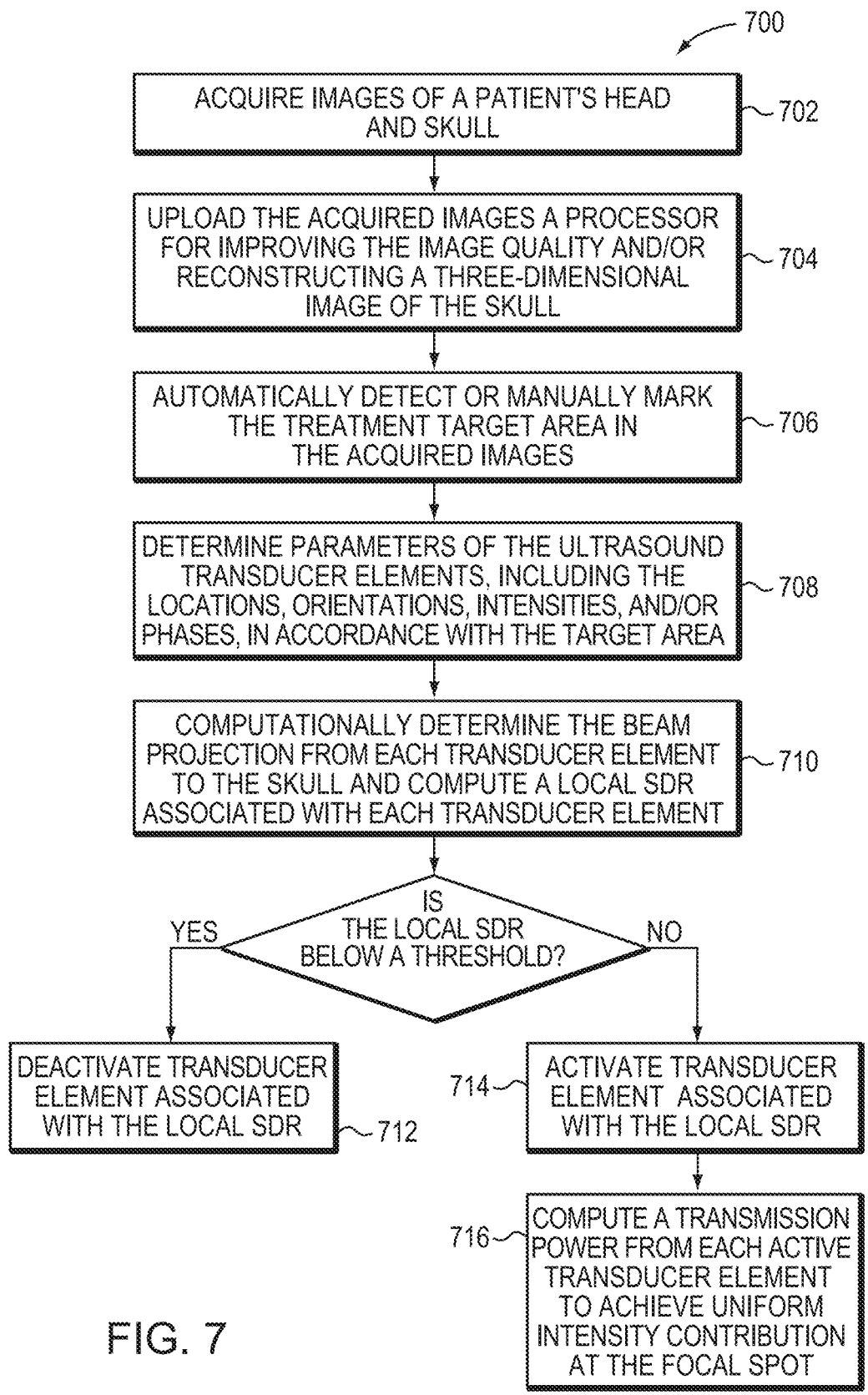
FIG. 7 is a flow chart illustrating an approach for obtaining uniform power distribution from each transducer element at the focus in accordance with various embodiments of the present invention.

A representative method 700 illustrating an approach for obtaining uniform power contributions from each transducer element at the focus in accordance with various embodiments of the current invention is shown in FIG. 7. In a first step 702, images of a patient's head and entire skull are acquired using the imager 112. In a second step 704, the acquired images are uploaded to the controller 108 that processes the images (e.g., by applying an imaging filter, such as a bone filter) to improve the image quality and reconstruct a three-dimensional image of the skull. In a third step 706, the treatment target area in the acquired images may be automatically detected or manually marked by an operator. In a fourth step 708, the controller 108 may determine parameters of the ultrasound transducer elements 104, including the locations, orientations, intensities, and/or phases, in accordance with the location of the target area such that the transducer elements 104 can collectively produce a focused ultrasonic beam at the target area. The controller 108 may then drive an actuator controlling the location and angular position of the transducer elements 104 based on the determined parameters. In a fifth step 710, the controller 108 may compute the beam projection from each transducer element to the skull based on the position of the element and the reconstructed three-dimensional image. The local SDR associated with each transducer element 104 can then be computed based on the beam projection on the skull. If the local SDR is below a threshold, the associated transducer element is deactivated (step 712). If the local SDR is above the threshold, the associated transducer element is activated (step 714). The transmission power from each active transducer element may be calculated in accordance with the formula as described above to achieve uniform intensity contribution at the focal spot (step 716).

The controller 108 used herein may be implemented in hardware, software or a combination of the two. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Although the present invention has been described with reference to specific details, it is not intended that such details should be regarded as limitations upon the scope of the invention, except as and to the extent that they are included in the accompanying claims. Accordingly, the described embodiments are to be considered in all respects as only illustrative and not restrictive.

What is claimed is:

1. A method of performing trans-skull ultrasound treatment for individual patients, the method comprising:
   obtaining a plurality of images of a patient's skull;
   detecting a treatment target area in the plurality of images;
   computationally determining a global skull density ratio (SDR) representing structural characteristics of the skull on a plurality of beam paths, each beam path extending from an ultrasound transducer element to the skull and focused at the treatment target area;
   determining a likelihood of successful trans-skull ultrasound treatment of the patient by comparing the global SDR to a predetermined threshold; and
   operating the ultrasound transducer elements based at least in part on the determined likelihood so as to improve effectiveness of the ultrasound treatment.

2. The method of claim 1, further comprising computationally determining a plurality of local parameters, each local parameter representing local structural skull characteristics on one of the beam paths, the global SDR being determined based on at least some of the local parameters.

3. The method of claim 2, further comprising assigning a weighting factor to each of the local parameters based on an incidence angle of the associated beam path through the skull, the global SDR being determined based on a weighted average of the at least some of the local parameters.

4. The method of claim 3, wherein a weighting factor of one is assigned to each local parameter corresponding to a beam path having an incidence angle smaller than a critical angle and a weighting factor of zero is assigned to each local parameter corresponding to a beam path having an incidence angle larger than the critical angle.

5. The method of claim 3, wherein the weighting factor is determined based on a logistic function.

6. The method of claim 5, wherein the logistic function satisfies an equation:

$$L_i = 1 - \frac{1}{1 + e^{-(\theta_i - \mu)/\sigma}},$$

where $L_i$ denotes the logistic function, $\theta_i$ denotes the incidence angle of the beam path from a transducer element i to the skull, $\sigma$ denotes a steepness factor representing deviation of a curve of the logistic function from a step function, and $\mu$ denotes an inflection point of the logistic function.

7. The method of claim 2, wherein the local parameter comprises a local skull density ratio.

8. The method of claim 7, herein the local skull density ratio is determined based on an intensity profile of the images.

9. The method of claim 1, wherein the images are acquired using at least one of a computer tomography (CT) device, a magnetic resonance imaging device, or an ultrasonography device.

10. The method of claim 1, wherein the ultrasound transducer elements are activated to perform the ultrasound treatment only when the determined global SDR exceeds the predetermined threshold.

11. A system for performing trans-skull ultrasound treatment for individual patients, the system comprising:
an ultrasound transducer array comprising a plurality of ultrasound transducer elements;
an imaging system for obtaining a plurality of images of a patient's skull; and
a controller, operably coupled to the ultrasound transducer array and the imaging system, configured to:
detect a treatment target area in the plurality of images;
computationally determine a global skull density ratio (SDR) representing structural characteristics of the skull on a plurality of beam paths, each beam path extending from one of the ultrasound transducer elements to the skull and focused at the treatment target area;
determine a likelihood of successful trans-skull ultrasound treatment of the patient by comparing the global SDR to a predetermined threshold; and
operate the ultrasound transducer elements based at least in part on the determined likelihood so as to improve effectiveness of the ultrasound treatment.

12. The system of claim 11, wherein the controller is further configured to computationally determine a plurality of local parameters, each local parameter representing local structural skull characteristics on one of the beam paths, the global SDR being determined based on at least some of the local parameters.

13. The system of claim 12, wherein the controller is further configured to assign a weighting factor to each of the local parameters based on an incidence angle of the associated beam path through the skull, the global SDR being determined based on a weighted average of the at least some of the local parameters.

14. The system of claim 13, wherein the controller is further configured to assign a weighting factor of one to each local parameter corresponding to a beam path having an incidence angle smaller than a critical angle and a weighting factor of zero to each local parameter corresponding to a beam path having an incidence angle larger than the critical angle.

15. The system of claim 13, wherein the controller is further configured to determine the weighting factor based on a logistic function.

16. The system of claim 15, wherein the logistic function satisfies an equation:

$$L_i = 1 - \frac{1}{1 + e^{-(\theta_i - \mu)/\sigma}},$$

where $L_i$ denotes the logistic function, $\theta_i$ denotes the incidence angle of the beam path from a transducer element i to the skull, $\sigma$ denotes a steepness factor representing deviation of a curve of the logistic function from a step function, and $\mu$ denotes an inflection point of the logistic function.

17. The system of claim 12, wherein the local parameter comprises a local skull density ratio.

18. The system of claim 17, wherein the controller is further configured to determine the local skull density ratio based on an intensity profile of the obtained images.

19. The system of claim 11, wherein the imaging system comprises at least one of a computer tomography (CT) device, a magnetic resonance imaging device, or an ultrasonography device.

20. The system of claim 11, wherein the controller is further configured to cause the ultrasound transducer elements to be activated only when the determined global SDR exceeds the predetermined threshold.

* * * * *